United States Patent [19]

Klein et al.

[11] 4,387,369
[45] Jun. 7, 1983

[54] BROAD SPECTRUM CHARGED ELECTRIC FIELD POLAR GAS SENSING AND DETECTION SYSTEM

[75] Inventors: Carl F. Klein, New Berlin; John E. Aukofer, Milwaukee, both of Wis.

[73] Assignee: Johnson Controls, Inc., Milwaukee, Wis.

[21] Appl. No.: 197,521

[22] Filed: Oct. 16, 1980

Related U.S. Application Data

[63] Continuation-in-part of Ser. No. 950,414, Oct. 11, 1978, abandoned.

[51] Int. Cl.$^3$ .............................................. G08B 17/10
[52] U.S. Cl. ..................................... 340/627; 340/628; 436/806; 324/61 R
[58] Field of Search ............... 340/627, 628, 632, 629, 340/634; 324/61 R, 61 P; 73/23, 23.1; 23/232 E

[56] References Cited

U.S. PATENT DOCUMENTS

| | | | |
|---|---|---|---|
| 3,221,248 | 11/1965 | Batteau et al. | 340/627 |
| 3,728,615 | 4/1973 | Hill et al. | 340/628 |
| 4,247,299 | 1/1981 | Klein et al. | 340/632 |
| 4,264,331 | 4/1981 | Klein et al. | 340/628 |

*Primary Examiner*—Gerald L. Brigance
*Attorney, Agent, or Firm*—Andrus, Sceales, Starke & Sawall

[57] ABSTRACT

An air pollutant and/or fire combustion sensing apparatus includes a capacitive sensor having spaced sensing electrodes producing a free space mounted within an environment subject to possible fire or the like. One of the sensing electrodes has an outer dielectric layer for absorbing contaminating gaseous products. The electrodes are connected to a high voltage power source for producing a charged capacitor with a high intensity static electric field of substantially $5 \times 10^5$ V/M up to the dielectric breakdown of air in the free space or gap. The electric field reacts upon the contaminating gaseous products of combustion and environmental pollution and produces an opposing electric field with a net change in the electric field and the summated voltage appearing across the electrodes. A high input impedance detecting circuit with good electrometer characteristics responds to the change in the field.

14 Claims, 2 Drawing Figures

BROAD SPECTRUM CHARGED ELECTRIC FIELD POLAR GAS SENSING AND DETECTION SYSTEM

BACKGROUND OF THE INVENTION

This is a Continuation-In-Part of the pending application Ser. No. 950,414, of Carl F. Klein et al, filed Oct. 11, 1978, now abandoned for "BROAD SPECTRUM CHARGED ELECTRIC FIELD POLAR GAS SENSING AND DETECTION SYSTEM".

This invention relates to a gaseous product detection system and particularly to an improved broad spectrum sensing capacitor unit for detecting environmental borne constituents generated as a result of combustion, pollution or the like.

Combustion detection and alarm systems employing various sensing and detecting means have been suggested, such as thermal, flame, photo-electric, ionization chamber, semi-conductors of a metal oxide or polymeric organic material, and electrolyte cell sensors. The various systems for detection and measurement of smoke have generally employed optical and ionization chamber devices, which, however, are generally capable of detecting only the particulate and liquid droplet concentration of the smoke. Optical sensors have been found to be the most effective large aerosol (10 microns) sensor, and ionization chambers the most effective small aerosol (1 micron) detector. The prior art optical and ionization chamber device are generally insensitive to smoke's gaseous components, including the noxious and toxic gases present in smoke.

A highly significant advance in the art is disclosed in the copending application, Ser. No. 821,515 entitled "Charged Non-Conductive Polar Gas Sensing Element and Detection System", filed on Aug. 3, 1977 and assigned to the same assignee as this application, wherein a sensing element includes a sensitive non-conductive surface material which is charged and has a characteristic to retain such charges.

The detection material is an electret which contains either electric dipoles and/or electric monopoles which develops a charge enhancing field. The sensing mechanism o the probe is two-fold in nature. The dielectric material performs as an adsorber of combustion products in combination with coulombic electrostatic forces created by the charge state of the material. Thus, the electric field associated with the electret material amplifies the adsorption and charge detection phenomena associated with non-charged dielectric materials. The electret's amplifications of its-non-charged adsorption capability would appear to be explained by the action of the electric field associated with the electret tending to align the adsorbed polar gas molecules, thus increasing the effect of their induced field. The electric field also has the ability to attract charged aerosols, ion radicals, and polar gas molecules. The degree of attraction associated with any such polar gas molecules which are present in the free space is of course dependent upon the degree the coulomb forces are able to overcome the thermal energy associated with the polar gases. The charged non-conductive or dielectric layer response to combustion products includes an initial pulse followed by a unique increasing ramp response function, apparently as the result of the electrostatic or field effect associated with the charged material. In addition with appropriate electrode placement, a capacitor sensor may be formed. In this embodiment, the electret field induces dipoles in the particulate matter which further modify the output signal of the probe means.

The most frequent cause of death of fire victims is due to noxious gases that find their way into the circulatory system and thereby poison and prevent an escape response by the victim. One of the most lethal gases emitted during the thermal degradation of the newer commercial polymeric materials is hydrogen cyanide. It is also produced when burning some of the older materials, such as wood and wool. When exposed to this gas via either inhalation or absorption through the skin, the fire victim usually dies rapidly. Victims that survive exposure may have residual dimentia or other neurological manifestations.

The gaseous products of combustion are, therefore, one of the products of combustion that present a great threat to the physiological processes of a fire victim. All UL approved fire detection devices, which are commercially available, rely only on the detection of concentrations of particulates and liquid droplets to sense the existence of a fire. The failure of existing systems to respond effectively and rapidly to the broad spectrum of the damaging constituents creates a significant area for development.

A detector unit which also includes significant response to both aerosols and toxic gas products during the combustion process would provide a significant improvement.

SUMMARY OF THE INVENTION

The present invention is directed to an environmental gaseous and particle detecting system utilizing a new detection mechanism, and in a preferred and a particularly unique embodiment having inputs responsive to two or more sensing mechanisms, each of which may measure a different product of combustion. An important aspect of this invention is that more than one type of combustion product can be measured.

The present invention is particularly directed to a relatively small integrated assembly for detecting airborne products such as smoke product detection using induced polarization in a specially formed high intensity electric field of a charged capacitive sensor which is connected to a charging power supply on at least an intermittent basis. The capacitor sensor is charged to create an electric field from substantially $2.6 \times 10^5$ V/M (volts per meter) to the dielectric breakdown of air, with a preferred minimum of $5 \times 10^5$ V/M. When smoke, including the aerosols and toxic gases, enters the electric field, the polar combustion molecules and particulates that have permanent dipole moments tend to align themselves in the electric field. Because the molecules are in constant thermal agitation, the degree of alignment will not be complete.

If the combustion molecules and particulates do not have permanent electric dipole moments, they are acquired by induction when placed in the capacitor's high intensity electric field. The induced electric dipole moment in the presence of the capacitor's electric field is detected. Smoke, as it enters the capacitor's field, becomes polarized. Generally, the uncharged smoke particles enter the air gap uncharged or neutral and remain neutral with positive induced charges equal in magnitude to negative induced charges. In this process, electrons in the smoke particles are displaced from equilibrium positions forming induced dipoles of polarization, $p = Nqd$. The induced smoke charge will always appear in such a way that the electric field set up by it ($E_s$)

opposes, the present high intensity electric field ($E_o$) of the capacitor. The resultant capacitor field E is the sum of $E_o$ and $E_s$ and has the same polarity as $E_o$ except for the fact that it is smaller due to the induced smoke polarization which tends to weaken the capacitor's original external field. The weakening of the capacitor's electric field reveals itself as a reduction in potential difference between the capacitor's plates.

BRIEF DESCRIPTION OF THE DRAWING

The drawing furnished herewith illustrates a preferred construction of the present invention in which the above advantages and features are clearly disclosed as well as others which will be clear from the following description of such embodiments.

In the drawing.

DESCRIPTION OF THE ILLUSTRATED EMBODIMENTS

Figure 1:
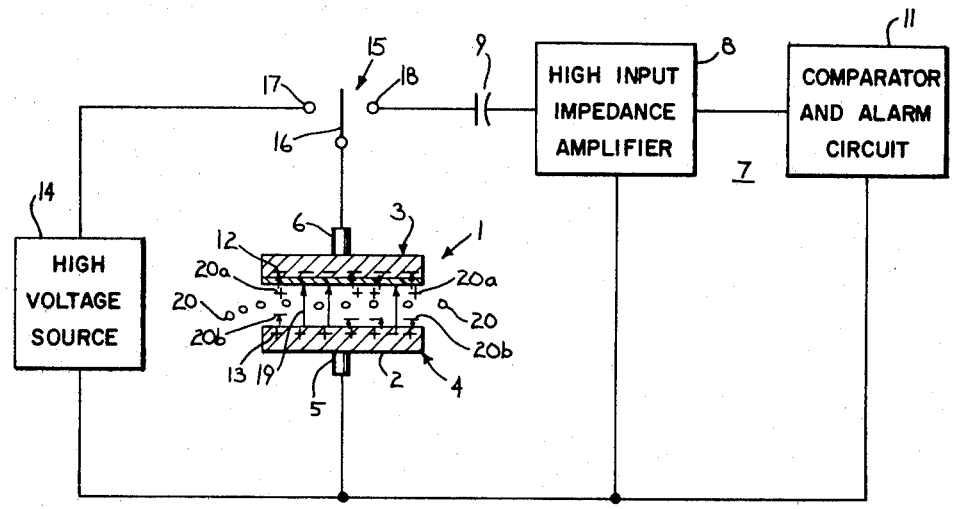
FIG. 1 is a view of a combustion product sensing unit in accordance with the present invention.

Referring to the drawing and, in particular, to FIG. 1, a sensing probe unit 1 constructed in accordance with the teaching of the present invention is shown including a pair of spaced capacitor plates 2 and 3 defining an air gap or free space 4 therebetween. Circuit terminals 5 and 6 are secured to the plates 2 and 3 and form a circuit connection means for connecting of the probe into a detection circuit. The unit 1 is connected as the input to a high impedance detection and processing circuit 7 which, as shown in FIG. , includes a signal coupling amplifier 8. The output of the capacitor plate 3 is coupled by a capacitor 9 to amplifier 8. The capacitor plate 3 is a metal plate which is preferably specially formed with a non-conductive surface 10 intimately secured to the surface facing the free space 4. Plate 3 is connected to the amplifier 8 of processing circuit 7 and operates a suitable alarm circuit 11 of any suitable construction.

In accordance with this invention, the capacitor unit 1 is charged to a high voltage on the order of 2000 volts or more, as shown by the positive and negative charge symbols 12 and 13 within the plates 2 and 3. The most significant fraction is the intensity of the electric field within the capacitor formed by plates 2 and 3. Although any charge will produce some effect, the inventors discovered that a field strength from substantially $2.6 \times 10^5$ V/M to the dielectric breakdown of air produces significant results and that a field strength or intensity of at least approximately $5 \times 10^5$ V/M produces more readily detected pollutant related signals, and in a practical installation with conventional high impedance detection apparatus, a field intensity of at least $10 \times 10^5$ V/M would be recommended as an optimum construction. The maximum field intensity will therefore vary with the environmental conditions including humidity, plate geometry and spacing and the like, all of which effect the dielectric breakdown of the air between the plates. These factors will be recognized by those skilled in the art and can of course be readily determined in a routine process. In the embodiment of FIG. 1, a high voltage D.C. source 14 is selectively connected to charge the capacitor unit 1. Thus, a single pole, double-throw switch 15 has a common pole 16 connected to capacitor plate 3 and alternately engageable with contacts 17 and 18. Contact 17 is connected to the source 14. Contact 18 is connected to capacitor 11 and thus the input of circuit 7. The plate of unit 1 is thereby selectively connected in the circuit with source 14 and circuit 7. An electric field 19 is thus created within the air gap 4. The apparatus of the invention was constructed with an electret and a spaced perforated ground shield. The plates were in one method connected to a constant D.C. voltage supply of 3400 volts and the spacing varied. The distance between the plates was varied in a practical sensing range to produce the following electric fields:

| SHIELD DISTANCE (d) | FIELD STRENGTH E = |
|---|---|
| 1/32″ = 7.94 × 10⁻⁴ meter | E = 4.28 × 10⁶ V/M |
| 1/16″ = 1.588 × 10⁻³ meter | E = 2.14 × 10⁶ V/M |
| ⅛″ = 3.175 × 10⁻³ meter | E = 10.7 × 10⁵ V/M |
| 3/16″ = 4.763 × 10⁻³ meter | E = 7.14 × 10⁵ V/M |
| ¼″ = 6.35 × 10⁻³ meter | E = 5.35 × 10⁵ V/M |
| 5/16″ = 7.94 × 10⁻³ meter | E = 4.28 × 10⁵ V/M |
| ⅜″ = 9.525 × 10⁻³ meter | E = 3.57 × 10⁵ V/M |
| 7/16″ = 1.11 × 10⁻² meter | E = 3.06 × 10⁵ V/M |
| ½″ = 1.27 × 10⁻² meter | E = 2.68 × 10⁵ V/M |

In another, the plate position was held constant and the voltage varied to obtain similar intensity electric fields. In each instance significant results were obtained. Although $2.68 \times 10^5$ V/M produced a detectable change, the results were not considered sufficient for reliable detection particularly in a practical environment. The difficulty is that below such a field intensity, the signal to noise ratio is such as to essentially prevent effective and reliable separation and detection of the pollutant related signal. Thus, at an intensity of $1 \times 10^5$ V/M, the pollutant related change in the signal was not detectible with the use of a high impedance amplifying system based on the current technology used for practical commercially available systems such as hereinafter set forth. This may thus be taken as a lower limit for practical application of the invention with current technology. Although highly sophisticated, and thus currently costly, filtering and amplifying systems might be used and may be necessary in the lower operating intensities to process the output signal with some detection, such as approach for all practical purposes severely limits and may prevent implementation of the invention in a practical operative installation. In the event of a fire, smoke or other combustion generated products, such as particles and/or gases, generally shown diagrammatically at 20, enter the air gap 4.

Generally, diagrammatically the products 20 function to generate an electric field, shown by charges 20a and 20b, which opposes that of the charges 12 and 13, with a resulting change in the electrical field and voltage signal across the capacitor probe 1. The voltage signal thus is an indication of the presence of gaseous products and particulates such as encountered in the incipient and following stages of combustion.

The present invention is directed to air borne product detection using induced polarization in a specially formed electric field of a highly charged capacitive sensor which is connected to a charging power supply on at least an intermittent basis. In the illustrated embodiment, the sensing electrode 3 includes coating 10 which may be a non-conductive plastic such as the well-known material sold by DuPont Co. under the trademark "TEFLON", an electret material such as disclosed in the cross-referenced application or the like. With the appropriate coating, the sensor will detect both particulate matter and gases. Without such coating, the sensor's major response is to particulate matter. Smoke includes both aerosols and toxic gases which enter the electric field in the free space between the two-spaced electrodes. The polar combustion molecules and particulates that have permanent dipole moments tend to align themselves in the electric field. Because the molecules are in constant thermal agitation, the degree of alignment will not be complete, but will increase as the applied electric field is increased. If the combustion molecules and particulates do not have permanent electric dipole moments, they are acquired by induction when placed in the capacitor's electric field. Smoke, as it enters the electric field thus becomes polarized. Generally, the uncharged smoke particles enter the air gap uncharged or neutral and remain neutral with positive induced charges equal in magnitude to negative induced charges. In this process, electrons in the smoke are displaced from equilibrium positions, forming induced dipoles of polarization, $P=Ngd$. The induced smoke charge will always appear in such a way that the electric field set up by it $E_s$ opposes the electric field $E_o$ of the capacitor. The resultant capacitor field E is the sum of $E_o$ and $E_s$ and has the same polarity as $E_o$ except for the fact that it is smaller due to the induced smoke polarization which tends to weaken the capacitor's original external field. The weakening of the capacitor's electric field reveals itself as a reduction in potential difference between the capacitor's plates. Here, $V=Ed$, where V=voltage, E=electric field strength and d=distance.

The induced polarization of a molecule in the smoke cloud can also be described with reference to its structure. If no external field is present, the molecule is in its normal electrical configuration. In the capacitor's electric field, the electron cloud shifts from its normal electrical configuration to a more deformed polar configuration. The shift is such that the force on the electron cloud by the electric field of the charged plates and the force on the electron cloud due to the coulombic attraction between the charges are balanced, and stable equilibrium exists.

$$F_E = F_C \quad \text{(Eq. 1)}$$

$$F_E = NqE \quad \text{(Eq. 2)}$$

and $F_C = (Nq)^2 d / 4\pi\epsilon_o R^3$ (Eq. 3)
Therefore, $$NqE = \frac{(Nq)^2 d}{4\pi\epsilon_o R^3} \quad \text{(Eq. 4)}$$

$$4\pi\epsilon_o R^3 E = Nqd \quad \text{(Eq. 5)}$$

The dipole moment of the molecule can therefore be written:

$$P = Nqd = 4\pi\epsilon_o R^3 E = \alpha E \quad \text{(Eq. 6)}$$

where $$\alpha = 4\pi\epsilon_o R^3 \quad \text{(Eq. 7)}$$

is the molecule's electronic polarizability. The polarizability $\alpha$ can be seen to depend not on the number of charges N of the molecule but rather on its radius R. One is therefore able to control the size of the particles being detected by controlling the magnitude of the electric field. The dipole moment can be seen to be proportional to the strength of the capacitor's electric field.

The phenomena may also be described including the induced polarization mechanism in terms of changes in a capacitor's relative permittivity. The passage of smoke forms a dielectric between the plates of a charged capacitor and will produce a change in the capacitor's relative permitivity. This change in permittivity will result in a change in the electric field intensity between the plates of the capacitor and thus, a change in the voltage across it. If no dielectric (smoke) is present, Gauss' Law states:

$$Q_c = Q_o = \epsilon_o \int E.ds = \epsilon_o E_o A \quad \text{(Eq. 10)}$$

$$E_c = E_o = \frac{Q}{\epsilon_o A} \quad \text{(Eq. 11)}$$

If the dielectric (smoke) is present, $$Q_c = Q_o - Q_i = \epsilon_o \int E.ds = \epsilon_o E_c A \quad \text{(Eq. 12)}$$

$$E_c = \frac{Q_o}{\epsilon_o A} - \frac{Q_i}{\epsilon_o A} \quad \text{(Eq. 13)}$$

$$\frac{Q_o}{A} = \epsilon_o E_c + \frac{Q_i}{A} \quad \text{(Eq. 14)}$$

$$D = \epsilon_o E_c + P_i \quad \text{(Eq. 15)},$$

wherein:

$D = Q_o/A$ is the electric flux density
$E = V/d$ is the electric field intensity
$P_i = Q_i/A$ is the induced polarization However, since $$D = \epsilon_o \epsilon_r E \quad \text{(Eq. 16)}$$

we can write $$D = \epsilon_o \epsilon_r E = \epsilon_o E + P_i \quad \text{(Eq. 17)}$$

$$P_i = \epsilon_o(\epsilon_r - 1)E \quad \text{(Eq. 18)}$$

or $$\epsilon_r = 1 + \frac{P}{\epsilon_o E} \quad \text{(Eq. 19)}$$

Since smoke detection is accomplished using induced polarization in a capacitor's electric field, the detector's particulate and liquid droplet sensitivity is proportional to the charge on the capacitor.

$$S \propto Q_c = Q_o - Q_i = DA = \epsilon_o \epsilon_r EA = \epsilon_o \epsilon_r \frac{V_A}{d} \quad \text{(Eq. 20)}$$

where
S = smoke sensitivity
D = the capacitor's electric flux density
A = capacitor's area
$\epsilon_o$ = permittivity of dielectric
$\epsilon_r$ = relative permittivity of dielectric
E = the capacitor's electric field intensity
V = the capacitor's voltage d = the spacing distance of the capacitor plates. From the above relationships, the most significant parameters of the new capacitor sensor unit is seen to include the following. The capacitor's area influences the magnitude of the capacitor's charge. The larger the capacitor's charge, the greater its electric field intensity. The amplitude of the capacitor's electric field intensity is also affected by the spacing distance between the capacitor's plates and the capacitor's voltage. Since the magnitude of the smoke particle's induced polarization or dipole moment is directly related to the capacitor's electric field intensity, as noted above, these factors provide direct influence and control on the detector's smoke sensitivity.

In addition, the dielectric layer 10 functions as an adsorber of gaseous molecules such that the sensor reponds to both contaminating particles and gases in the environment.

By use of an appropriate circuit 7, the voltage signal can be detected. The electronic processing circuit 7, may of course, be of any suitable construction adapted to provide a high impedance input connection to the capacitive unit 1 such as generally disclosed in the previously identified application and also in U.S. Pat. Nos. 3,989,463 and 3,754,219.

The capacitor unit 1 is charged to a high voltage to produce the desired electric field and the resulting significant, unique response to the products of combustions including those created during the incipient and initial stages. The circuit 7 must be constructed to receive the high voltage signal, or the input must employ an appropriate high voltage isolating means, such as the coupling capacitor 11.

Figure 2:
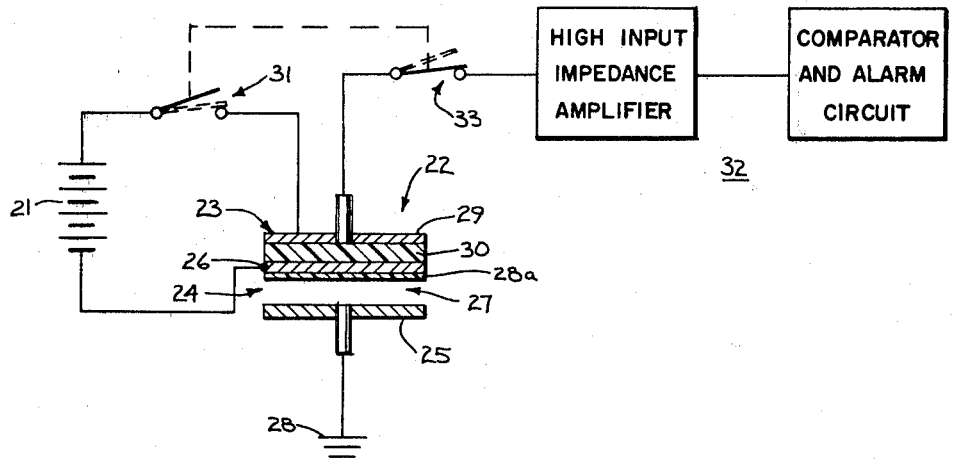
FIG. 2 is a view of an alternate embodiment.

A further preferred embodiment of this invention is shown in FIG. 2 wherein a source of high voltage shown by a conventional D.C. battery 21 is periodically connected to charge a multilayered capacitor unit 22 having a special capacitor section 23 and a free space capacitor section 24 to create a high intensity electric field which should have at least an intensity of substantially $2.6 \times 10^5$ V/M or greater. Section 24 includes a pair of spaced capacitor plate elements 25 and 26 with a sensing air gap or free space 27 between the plates within which the smoke or other environmental borne products freely enter. Plate 25 is connected to circuit common shown as ground 28, while plate 26 is connected to and also forms a part of the capacitor section 23. Plate 26 may also be provided with a suitable outer-nonconductive layer of "TEFLON" or other suitable material 28a. The capacitive section 23 includes a second plate 29 which is separated from and capacitively coupled to plate 26 by a suitable dielectric 30. The second plate 29 is connected by a switch 31 to the high voltage source 21 and alternately to the appropriate signal processing system 32 by a switch 33. Switches 31 and 32 may be ganged or interlocked to alternately connect the plate 29 to source 21 and system 32. The opposite plate 26 is connected directly to the return side of the voltage source, and thus the charge is applied to the capacitive section 23 only.

The charging period is determined by the rate of charge leakage from the capacitor unit 23 and 27. During charging, the signal processing means 32 is disconnected so as to isolate the detection circuitry from the high voltage charging source 21. After charging, the source 21 is disconnected to permit the charge measurement without interference from a low impedance, such as a battery. The input to system 32 is connected to the charge on the capacitor's plate is monitored for variations in its charge due to induced smoke polarization in the second capacitor's air gap 27. The induced smoke polarization again produces an electric field opposing that of the charged capacitor plates and is coupled through the outer capacitor to the signal processing means 32. The multicapacitor embodiment isolates the high voltage charge source from the signal processing circuitry.

The present invention thus provides a unique capacitive sensor for detecting pollutant and combustion products.

Although shown with the surface material attached to the opposite faces of a plate-like element, other configurations can, of course, be employed. The elements may, for example, be perforated to further provide for movement into and through the free space, and other than plate-like support members, may be readily employed. An important aspect of this invention is the exposure of the gaseous products and the airborne particles to a significant surface area of the uniquely charged dielectric material in combination with a means to detect the charge characteristic associated with the absorbed gas molecules. In relatively large areas, a plurality of units may be distributed through out the area and connected to a single processing circuit or to individual processing circuits. The present invention thus further enhances the response of a sensor employing a non-conductive sensitive surface by producing a sensor more fully responsive to both particulate matter and gases in an environment, such as smoke and the like, while maintaining a relatively low cost unit having a long, reliable life. The invention can be employed in any gaseous environment in which the products generated interact with the special charged surface means to provide a change in the surface charge.

Various modes of carrying out the invention are contemplated as being within the scope of the following claims particularly pointing out and distinctly claiming the subject matter which is regarded as the invention.

We claim:

1. An environmental gaseous product sensing apparatus creating an electrical signal in the presence of environmental borne contaminating products including particles and gaseous products, comprising a first and second sensing plate means each having an extended exposed sensing surface and being closely spaced to define a free space between said exposed sensing surfaces, means for mounting of the plate means exposed to contact with the surrounding environment in which said contaminating products may arise, an electrical detection means having a high input impedance amplifier connected to said first and second plate means, means defining a high voltage charge source having an output voltage of approximately 2,000 volts, switch means connected to said detection means and to at least one of said plate means and to said charge source for creating a high voltage charge on said plate means and disconnecting the charged plate means from the source during connection to said detection means, said charge producing a high intensity electric field between said plate means with said source disconnected from said plate means, said field having an intensity selected to induce polarization of particles and gaseous products in said contaminating products between said plate means and within said field, said induced polarization of said products in said free spacing producing an opposing field and with said high intensity electric field producing a changing electric field and thereby producing a detectable electrical output at the detection means related to the environmental borne contaminating products.

2. The sensing apparatus of claim 1 wherein said one plate means includes a dielectric layer defining said exposed surface exposed to said free space.

3. The apparatus of claim 1 wherein said one plate means includes a base conductor mounted in spaced relation to the second plate means and having a dielectric material layer intimately attached to said base conductor, an outer capacitor conductor plate intimately attached to said dielectric layer, said outer capacitor conductor and said base plate being connected to said charge source and to said first output means.

4. The apparatus of claim 3 wherein said conductor plate has a dielectric layer defining said exposed surface exposed to said free space.

5. A method of detecting environmental borne contaminating particles and products in a gaseous sample comprising, forming a free space defined by first and second sensing surfaces of first and second sensing probes, periodically applying a high voltage source of approximately 2,000 volts to the sensing surfaces and generating a high intensity electric field therebetween, periodically disconnecting the high voltage source from the sensing plate and switching the outputs of the sensing probes to a detection means, passing a gaseous test sample suspected of containing environmental borne contaminating particles and products through said free space when the high voltage source is disconnected, contacting said gaseous sample with said sensing surfaces and the high intensity electric field, said electric field polarizing said particles and gaseous product within the electric field to establish an opposing electric field and thereby generating an electric signal indicative of a changing electric field due to said high intensity field and said induced opposing electric field, amplifying said generated signal in said detection means by passing said signal through a high impedance amplifier and transmitting the amplified signal to an output means in said detection means for indicating the presence of said environmental particles and products.

6. An environmental gaseous product sensing apparatus creating an electrical signal in the presence of environmental borne contaminating products including particles and gaseous products, comprising a first and second sensing plate means each having an extended exposed sensing surface and being closely spaced to define a free space between said exposed sensing surfaces, means for mounting of the plate means exposed to contact with the surrounding environment in which said contaminating products may arise, an electrical detection means having a high input impedance amplifier connected to said first and second plate means, means defining a high voltage charge source, a switch means connected to said detection means and to at least one of said plate means and to said charge source for creating a high voltage charge on said plate means and disconnecting the charged plate means from the source during connection to said detection means, said charge source creating an electric field having a high intensity of at least $1 \times 10^5$ V/M, said charge producing said high intensity electric field between said plate means with said source disconnected from said plate means, said field intensity inducing polarization of particles and gaseous products in said contaminating products between said plate means and within said field, said induced polarization of said products in said free spacing producing an opposing field and with said high intensity electric field producing a changing electric field and thereby producing a detectable electrical output at the detection means related to the environmental borne contaminating products.

7. The apparatus of claim 6 wherein said intensity is in a range of from substantially $2.6 \times 10^5$ V/M to the dielectric breakdown of the environment in said free space.

8. The apparatus of claim 7 wherein said charge is selected to establish a field intensity of at least $5 \times 10^5$ V/M.

9. The sensing apparatus of claim 6, 7 or 8 wherein said first plate means includes a dielectric layer on a surface exposed to said free space.

10. The apparatus of claim 6, 7 or 8 wherein said first plate means includes a base conductor mounted in spaced relation to the second plate means and having a dielectric material layer intimately attached to said base conductor, an outer capacitor conductor plate intimately attached to said dielectric layer, said outer capacitor conductor plate and said base plate being connected to said charge source and to said first output means.

11. The apparatus of claim 10 wherein said capacitor conductor plate has a dielectric layer on a surface exposed to said free space.

12. The apparatus of claim 6 wherein said switch means includes first switch means connected between the plate means and the charge source and second switch means connected between the plate means and the detection means to alternately connect the charge source and the detection means to the plate means.

13. A method of detecting environmental borne contaminating particles and products in a gaseous sample comprising, forming a free space defined by first and second sensing surfaces of first and second sensing probes, periodically applying a high voltage source to the sensing surfaces and generating a high intensity electric field having an intensity of at least $5 \times 10^5$ V/M within said free space between said sensing surfaces, periodically disconnecting the high voltage source from the sensing probes and switching the outputs of the sensing probes to a detection means, passing a gaseous test sample suspected of containing environmental borne contaminating particles and products through said free space when the high voltage source is disconnected from said sensing probes, contacting said gaseous sample with said sensing surfaces and the high intensity electric field, said electric field polarizing said particles and gaseous product within the electric field to establish an opposing electric field and thereby generating an electric signal indicative of a changing electric field due to said high intensity field and said induced opposing electric field, amplifying said generated signal in said detection means by passing said signal through a high impedance amplifier and transmitting the amplified signal to an output means for indicating the presence of said environmental particles and products.

14. The method of claim 13 wherein said field intensity is at least $10 \times 10^5$ V/M.

* * * * *

UNITED STATES PATENT AND TRADEMARK OFFICE
CERTIFICATE OF CORRECTION

PATENT NO. : 4,387,369
DATED : June 7, 1983
INVENTOR(S) : Carl F. Klein, John E. Aukofer It is certified that error appears in the above-identified patent and that said Letters Patent is hereby corrected as shown below:

Column 3, Line 33, After "Fig." there should be "1"

Column 6, Line 8, Cancel "permitivity" and substitute therefor --- permittivity ---

Column 8, Line 1, Cancel "to", in the second occurrence, and substitute therefor --- and ---

Signed and Sealed this

Seventeenth Day of January 1984

[SEAL]

Attest:

GERALD J. MOSSINGHOFF

Attesting Officer

Commissioner of Patents and Trademarks